(12) United States Patent
Finger

(10) Patent No.: US 8,690,747 B2
(45) Date of Patent: Apr. 8, 2014

(54) EYELID PLAQUE

(71) Applicant: Paul T Finger, New York, NY (US)

(72) Inventor: Paul T Finger, New York, NY (US)

( * ) Notice: Subject to any disclaimer, the term of this patent is extended or adjusted under 35 U.S.C. 154(b) by 0 days.

(21) Appl. No.: 13/787,081

(22) Filed: Mar. 6, 2013

(65) Prior Publication Data
US 2013/0253251 A1 Sep. 26, 2013

Related U.S. Application Data

(62) Division of application No. 12/069,820, filed on Feb. 13, 2008, now Pat. No. 8,414,467.

(51) Int. Cl.
*A61N 5/00* (2006.01)

(52) U.S. Cl.
USPC .............................. 600/3; 600/218; 600/236

(58) Field of Classification Search
USPC .................. 600/1–8, 184, 190, 196, 201–216, 600/218–223, 235, 236
See application file for complete search history.

(56) References Cited

U.S. PATENT DOCUMENTS 6,443,881 B1 * 9/2002 Finger ............................... 600/1

* cited by examiner

Primary Examiner — Charles A Marmor, II
Assistant Examiner — Carrie R Dorna
(74) Attorney, Agent, or Firm — William B. Gowanlock

(57) ABSTRACT

An eyelid plaque and a method of using the plaque to treat eye cancers. The eyelid plaque is placed on the eyelid such that it defines an enclosure within which the radiation source resides. The enclosure defines a radiation shield that reduces radiation entering other organs and structures proximate the cancer being treated.

4 Claims, 5 Drawing Sheets

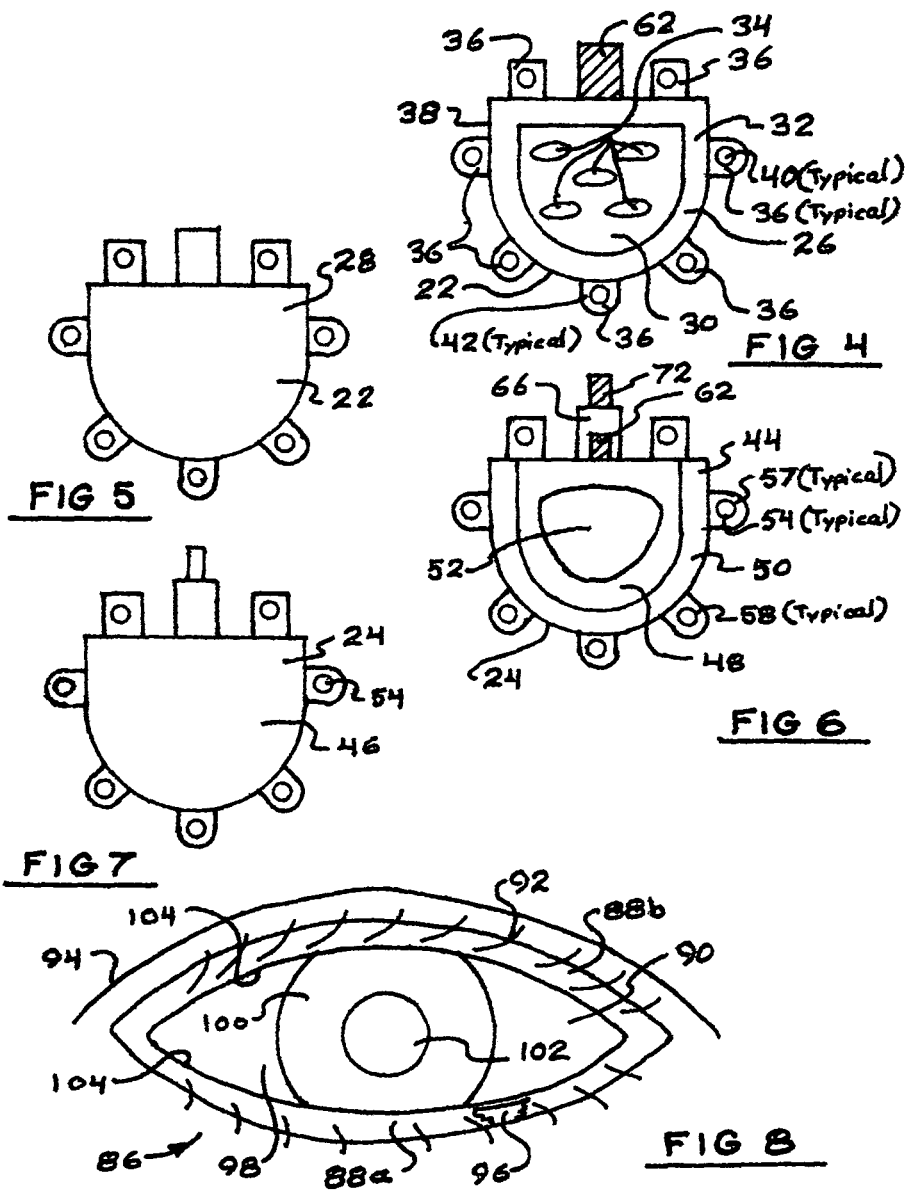

EYELID PLAQUE

CROSS-REFERENCE TO RELATED APPLICATIONS

This application is a divisional application of U.S. patent application Ser. No. 12/069,820 entitled "Eyelid Plaque," filed Feb. 13, 2008. The complete disclosure of which is hereby fully incorporated by reference.

FIELD OF THE INVENTION

The present invention relates to a medical device and its use. More specifically, the medical device is an eyelid plaque that may be used to treat eyelid cancers.

BACKGROUND

One of the structures of the human eye is the eyelid. A medical condition that may afflict eyelids is cancer, as more than one type of cancer may afflict eyelids, the cancers are generally referred to as eyelid cancers.

Human eyelids consist of an upper eyelid and a lower eyelid. The upper and lower eyelids cooperate to conceal or expose a portion of an underlying eyeball. In performing this function, the lower eyelid has relatively little movement, while the upper eyelid acts much like a shade. The shade action is facilitated by what is commonly known as a "crease," which permits some of the eyelid to overlap itself when the eyeball is exposed. The crease varies depending upon ethnic background. For example, the upper eyelids of people with an Asian background tend not to have a pronounced "crease," which is found in people with a Western background.

An eyelid has two opposing surfaces—a visible external surface, i.e., skin, and a non-visible interior surface, i.e., a tarsal plate, which "rides" on the eyeball. Between these two opposing surfaces, or structures, within the eyelid are various other structures, such as muscle and fat. The eyelids also have eyelashes. It is possible with either eyelid to pull the eyelid away from the underlying eyeball to create a gap.

Eyelid cancer is a general term for any cancer that occurs on, or within, the eyelids, upper or lower. Malignant eye cancers include basal cell carcinoma, sebaceous carcinoma, squamous cell carcinoma, and melanoma.

Eyelid cancers occur in multiple structures of the eyelids. More specifically, basal cell carcinoma is found under the squamous cells in the lower epidermis, which is the outer layer of the skin. Sebaceous carcinoma is found in the meibomian glands and the glands of Zeis. Squamous cell carcinoma is found in the squamous cells, which are located in the lower epidermis. Melanomas are found in the deepest layers of the epidermis.

Eyelid cancers are staged (or quantified) by the TNM system. Under the TNM system, a cancer can be staged as a TX, T0, Tis, T1, T2, T3, or T4 cancer. Associated with the T1, T2, and T3 designations are size limitations. A T1 stage cancer has a cancer growth of 5 mm or smaller in diameter, or is not invading the tarsal plate. A T2 stage cancer is between 5 mm and 10 mm, or has invaded the tarsal plate. A T3 stage cancer is greater than 10 mm, or has spread into the full thickness of the eyelid.

Treatment options for eyelid cancers are based on the type of cancer and the stage. Treatment options include surgical removal, such as surgical biopsy (e.g., incisional or excisional), Mohs' surgery, or cryosurgery. Non-surgical options include using high-energy x-rays from a machine outside the body to bombard the cancer. A radiation/surgical option is brachytherapy (i.e., surgical implantation of radioactive material in the cancer).

Each procedure has its own side effects. Surgical procedures may result in infection, pain, and the need for plastic surgery, such as for reconstruction or for changes in eyelid position. Side effects of radiation treatments not only include infection, pain and potentially the need for plastic surgery, but also rashes, dry skin, skin color change, cataract development, loss of eyelashes and/or dry eye, red eye, tearing, sensitivity to light, retinopathy, optic neuropathy, and neovascular glaucoma. Some complications from radiation treatments can lead to the need to remove the eye.

Despite the potential complications, radiation treatment of eyelid cancers is an efficacious treatment that offers the potential to avoid plastic surgery, which is common with a surgical procedure. Therefore, where an eyelid cancer is susceptible to radiation treatment, a radiation treatment would be preferred if the undesirable side effects could be reduced or eliminated. As a result, what is needed in the art is a better method of delivering radiation to an eyelid cancer so that damage to other organs, such as the eye, is at least minimized.

SUMMARY OF THE INVENTION

The invention is an eyelid plaque and a method of using the eyelid plaque to treat eyelid cancers. The eyelid plaque is placed on the eyelid such that it defines an enclosure within which a radiation source resides. The enclosure defines a radiation shield that reduces radiation exiting the eyelid plaque and entering other organs and structures proximate the cancer being treated. The eyelid plaque remains in place for several days, which may allow for the use of low doses of radiation over a longer period to treat any given cancer.

These and other features, aspects, and advantages of embodiments of the present invention will become apparent with reference to the following description in conjunction with the accompanying drawings. It is to be understood, however, that the drawings are designed solely for the purposes of illustration and not as a definition of the limits of the invention.

BRIEF DESCRIPTION OF THE DRAWINGS

FIG. 4 is a side view drawing of a first side of a first body taken along line 4-4 shown in FIG. 3.

FIG. 5 is a side view drawing of a second side of the first body taken along line 5-5 in FIG. 3.

FIG. 6 is a side view drawing of a first side of a second body taken along line 6-6 in FIG. 3.

FIG. 7 is a side view drawing of a second side of the second body taken along line 7-7 in FIG. 3.

FIG. 8 is a front view drawing of an eye having eyelashes with an eye cancer depicted on the lower eyelid of the eye.

DETAILED DESCRIPTION

FIGS. 1-7 depict an eyelid plaque of the present invention. A "plaque" as used herein means a medical device with which radiation is commonly associated. An example of a medical plaque is the plaque used in a procedure known as Plaque Brachytherapy, which is a procedure, used to treat cancers on, or within, an eyeball.

Figure 1:
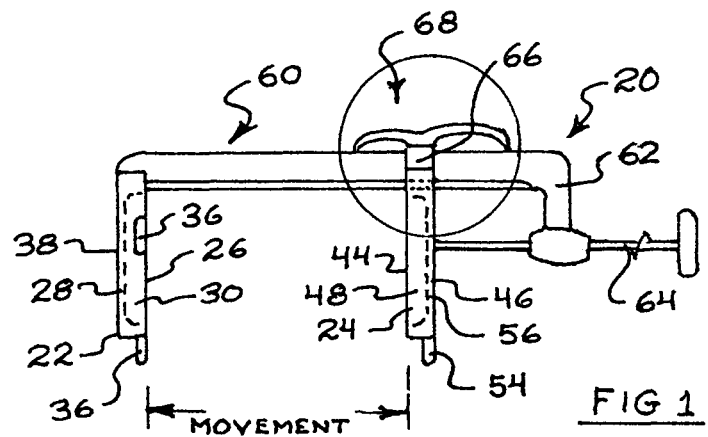
FIG. 1 is a side view drawing of an eyelid plaque of the present invention.
Figure 3:
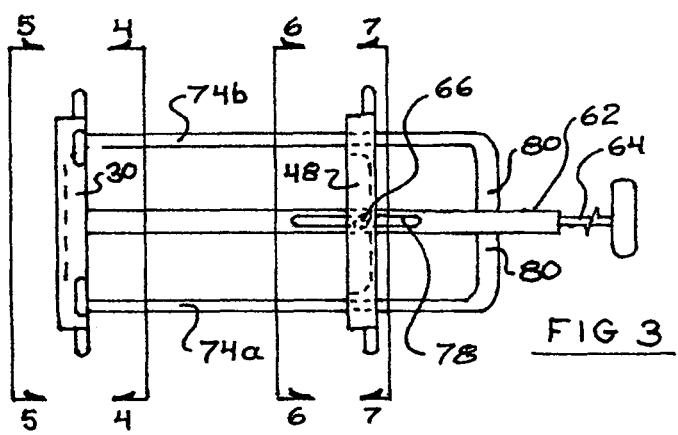
FIG. 3 is a top view drawing of the eyelid plaque depicted in FIG. 1.

As shown in FIG. 1, the eyelid plaque, generally referred to by reference number 20, includes a first body 22 and a second body 24.

Referring to FIGS. 1, 4 and 5, the first body 22 has a front surface 26 and a back surface 28. The first body 22 defines a first depression 30 in the front surface 26, creating a rim 32. In use, the first depression 30 may have positioned therein a radiation source 34, which is illustrated as a plurality of seeds.

The first body 22 has attachment points 36. The attachment points 36 are illustrated as a series of tabs extending outwardly from the first body's exterior surface 38. As the illustrated attachment points 36 are intended for use with sutures, each attachment point defines a through hole 40, which allows a suture to be placed through the attachment point. Each attachment point 36 ideally has a surface 42 in the same plane as the rim 32, such that when the attachment point is used to secure the first body 22 to a surface, such as an eyelid (not shown), pressure is evenly distributed on the surface and rim to the surface.

Continuing with FIGS. 1, 6 and 7, the second body 24 has a front surface 44 and a back surface 46. The second body 24 defines a second depression 48 in the front surface 44, creating a rim 50. In use, the second depression 48 may have positioned therein a radiation source 52, which is illustrated as a solid mass.

The second body 24 has attachment points 54. The attachment points 54 are illustrated as a series of tabs extending outwardly from second body's exterior surface 56. As these attachment points 54 are intended for use with sutures, each attachment point defines a through hole 57, which allows a suture to be placed through the attachment point. Each attachment point 54 ideally has a surface 58 in the same plane as the rim 50, such that when the attachment point is used to secure the second body 24 to a surface, such as an eyelid (not shown), pressure is evenly distributed on the surface and rim to the surface.

In use, the first body 22 and the second body 24, with a body (e.g., an eyelid) therebetween, should cooperate to define an enclosure. More specifically, at least one of the two bodies 22, 24 will have a radiation source positioned therein. It is important that in use that the enclosure created by the first body 22, the second body 24 and the body therebetween confine that radiation to the maximum extent practical. To accomplish this, the first body 22 and the second body 24 should generally align (e.g., at the rims 32, 50), in the direction of closure. The term 'generally align" means that in the direction of closure the first body 22 and the second body 24 would have continuous contact, if contact were possible. Is should also be appreciated that in the case where only one of the bodies 22, 24 has a depression, the other body may have a flat front surface; thus, in that case "generally align" would mean that the rim of one of the bodies would align with the flat surface of the other. The better the alignment, the better radiation leakage will be controlled. Contouring of the front surfaces in other planes, which would prevent actual contact of the rims, for an application will be discussed below.

Figure 2:
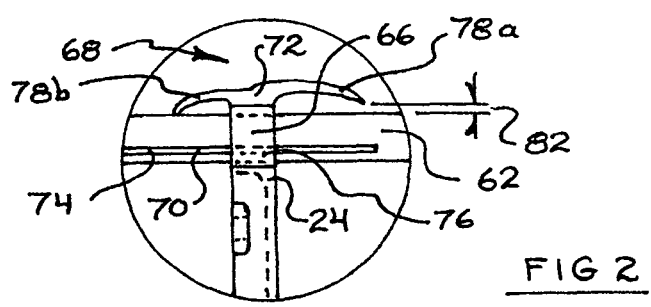
FIG. 2 is an expanded view drawing of a portion of the eyelid plaque depicted in FIG. 1.

Referring to FIGS. 1 and 2, the first body 22 and the second body 24 may have an adjustable connection, generally referred to by reference number 60, permitting the first body 22 and the second body 24 from an initial position of being apart to be controllably brought closer together. The adjustable connection 60 has the benefit of structurally unifying the first body 22 and second body 24 making it easier to use the eyelid plaque 20. At some point when the first body 22 and the second body 24 are brought closer, the adjustable connection 60 opposes the first depression 30 and the second depression 48, and generally aligns the first body 22 and the second body 24. As illustrated, the depressions 30, 48 are always opposed. It is also desirable to be able to use the adjustable connection 60 to move the first and second bodies 22, 24 apart.

The adjustable connection 60 includes a bar 62 and an adjustor 64. The bar 62 is fixedly connected to the first body 22. The second body 24 is slidably connected to the bar 62 by a slide 66, which permits movement of the second body along the bar. The bar 62 and slide 66 should have cooperating non-rotational cross-sectional shapes (e.g., not round) that fixes at least one aspect of the spatial relationship (e.g., the general alignment) between the first body 22 and the second body 24. As illustrated, the bar 22 and slide 66 have a rectangular cross-section and rectangular opening, respectively; therefore, the second body 24 cannot rotate about the bar.

Affixed to the back surface 46 of the second body 24 and the bar 62 is the adjustor 64, illustrated as a screw. The adjustor 64 permits controllable movement, which in the case of screw is also continuous, of the second body 24 along the bar 62, at least within the direction of the first body 22. While it is anticipated that a structure, such as an eyelid, will be positioned between the first body 22 and the second body 24, which is discussed below, the adjustable connection 60 should be capable of bringing both bodies together. It should be appreciated that the adjustor 64 may be capable of moving both bodies 22, 24 apart, to the degree permitted by the travel available from the bar 62. The travel distance between the first body 22 and the second body 24 is application dependent.

The eyelid plaque 20 may also contain a stability mechanism, generally referred to by reference number 68, to maintain, or assist in maintaining, the general alignment of the first body 22 and the second body 24. Thus, ideally when the two bodies 22, 24 are brought together with a portion of a structure, such as an eyelid, therebetween, the two bodies 22, 24 create a better enclosure than might otherwise be possible; thereby further limiting radiation leakage from the eyelid plaque 20.

The stability system 68 includes both rotational elements 70 and longitudinal elements 72. The rotational elements 70 include at least one rail 74 (two rails are illustrated) wherein the at least one rail is offset from the bar 62. The rotation elements 70 may either supplement the non-rotational aspects of the bar 62 and slide 66 in maintaining an aspect of the spatial relationship between the first body 22 and the second body 24, or provide the structure that maintains the spatial relationship. The rotational elements 70 provide opposing moments to assure that the second body 24 is restricted, or further restricted, from rotation about the bar 62.

The at least one rail 74 is connected between the second body 24 and the bar 62 in such a way that as the second body travels up and down the bar, the second body travels up and down the at least one rail. As illustrated, the rails 74a, b are parallel with the portion of the bar 62 on which the second body 24 travels. Each at least one rail 74 is affixed at one end to the first body 24 and at the other end to the bar 62. Intermediate between the affixed ends of the each offset rail 74, the offset rail passes through a guide 76 affixed on the second body 24.

Referring to FIGS. 1 and 2, the longitudinal element 72 includes at least one beam 78. The at least one beam 78 is connected to the second body 24, as illustrated on the slide 66, and extends therefrom along the bar 62, which permits the at least one beam 78 to travel along the bar 62 with the second body.

As illustrated, one beam 78a extends outwardly in one direction from the second body 24 and one beam 78b extends outwardly from the second body in the opposite direction. The longer the length of the at least one beam 78, the better it will be at controlling the swing of the second body 24. Each at least one beam 78 has a terminal end 80 that contacts the bar 62.

Figure 12:
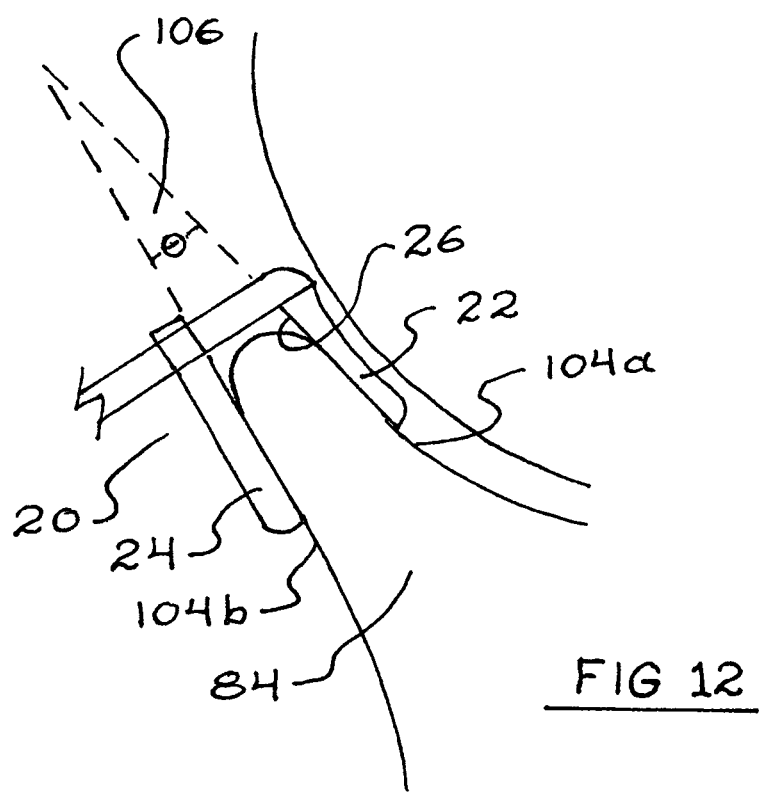
FIG. 12 is a side view drawing of the eye of FIG. 9 showing an eyelid plaque with still other limitations.

A small gap 82 may be present at the terminal end 80 of the at least one beam 78 and the bar 62. The gap 82 allows for some swing of the second body 24 relative to the first body 22 to accommodate clamping about surfaces that are not parallel. More specifically, as shown in FIG. 12, when the eyelid plaque 20 is used with an eyelid 84, the eyelid does not have parallel sides. This aspect of the invention is discussed in detail below.

The first body 22 and the second body 24 of the eyelid plaque 20 should be made from, or incorporate, materials that provide radiation shielding, such as gold. More specifically, if the bodies 22, 24 are not made entirely from radiation blocking materials, radiation-blocking materials should be incorporated within each body in such a way as to make each body an effective radiation shield. For, in use, the first body 22 and second body 24 cooperate to define an enclosure, and one of the primary requirements of the enclosure is to minimize the escape of the radiation therefrom to avoid collateral damage to other tissues.

The eyelid plaque 20 may have variations from the above-discussed eyelid plaque. For example, radiation need not be associated with each body 22, 24. More specifically, a cancer treatment may only require radiation be placed within one body. When radiation is not placed in a body, the body need not define a depression. Other variations in the structure are discussed below within the context of employing the eyelid plaque 20 to treat an eyelid cancer.

FIG. 8 is a front view drawing of an eye, generally referred to by reference number 86, having eyelids 88 (lower 88a and upper 88b), eyeball 90, eyelashes 92 and an upper eyelid crease 94 with an eyelid cancer 96. The structures of the eyeball 90 are the sclera 98, iris 100, and pupil 102. Each of the eyelids 88 has a perimeter 104 (lower 104a and upper 104b). The eyelid cancer 96 is depicted on the lower eyelid 88a of the eye 86.

Figure 9:
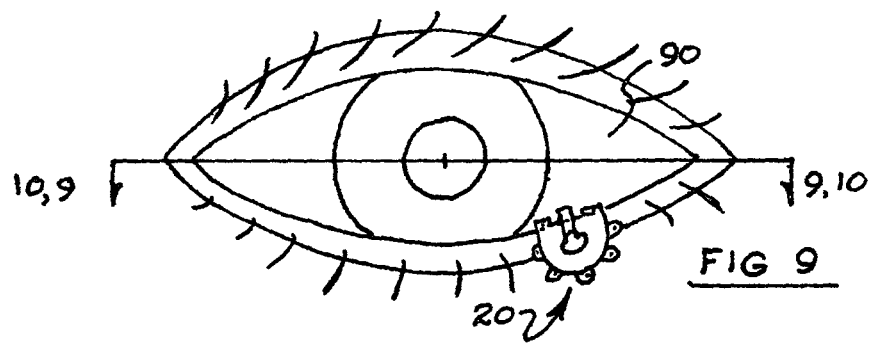
FIG. 9 is front view drawing of the eye of FIG. 8 having an eyelid plaque positioned over the eyelid cancer.

As shown in FIG. 9, an eyelid plaque 20 is attached to the lower eyelid 88a to treat the eyelid cancer shown in FIG. 8. This illustrative example of using an eyelid plaque 20 to treat an eyelid cancer assumes that the eyelid cancer requires radiation treatment from both sides of the eyelid. Thus, both the first body 22 and the second body 24 define a depression 30, 48 and radiation has been placed within each. The illustrated Eyelid plaque 20 also includes an adjustable connection 60 and stabilizing system 68.

Figure 10:
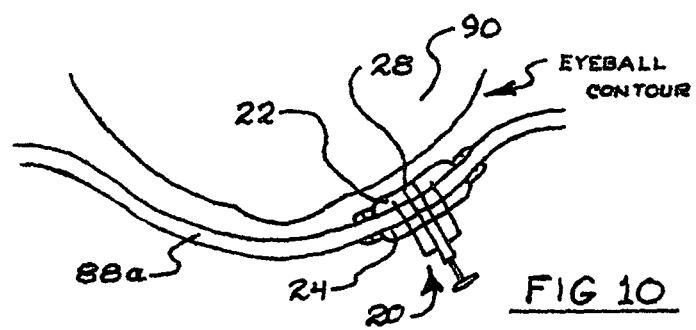
FIG. 10 is a top view drawing of the eye of FIG. 9.

Continuing with FIGS. 9 and 10, in this illustrative example, attachment of the eyelid plaque 20 is accomplished by placing the first body 22 in a gap between the eyelid 88a and the eyeball 90. Then, using the adjustable connection 60 the second body 24 was moved toward the first body 22, effectively "clamping" the eyelid plaque 20 to the eyelid 88. Ideally, only the first body 22 and second body 24 should contact the eyelid 88. Other structures of the eyelid plaque 20, such as the adjustable connection 60 and stability system 68, should not contact the eyelid.

The first body 22 and the second body 24 may be attached to the eyelid 88a; for example, by suturing (not shown) using the attachment points 36, 54. After attachment of the first body 22 and the second body 24 to the eyelid 88a, pressure on the eyelid 88a from the eyelid plaque 20, resulting from clamping should be released.

As shown in FIGS. 9 and 10, substantially all the first body 22 is within the gap. As used here, the term "substantially all" means that there is only an incidental amount, if any, of the first body 22 that is not within the gap.

As those skilled in the treatment of eyelid cancer will appreciate, the above disclosure broadly teaches an apparatus having a first body 22 and a second body 24 that cooperate to define an enclosure having and confining radiation therein. As illustrated, an application for this apparatus is the treatment of an eyelid cancer. Thus, the additional features of the eyelid plaque 20, such as the adjustable connection 60, merely provide additional structure to better position the first body 22 and second body 24 relative one to the other when used in an application to better confine the radiation. In addition, where the eyelid plaque 20 is used for treating an eyelid cancer it must be sufficiently light in weight to be tolerated by a patient, because as previously discussed, the eyelid plaque will remain on the eyelid for several days.

Continuing with FIG. 10, the back surface 28 of the first body 22 has been countered to the contour of the eyeball 90. More specifically, the adult human eyeball has a diameter of about 25 mm. Non-adult human eyeballs are about 75 percent the size of an adult human eyeball The eyelid perimeter is consistent with these dimensions. The back surface 28 therefore may be concave having a curvature consistent with the curvature of the eyeball.

Figure 11:
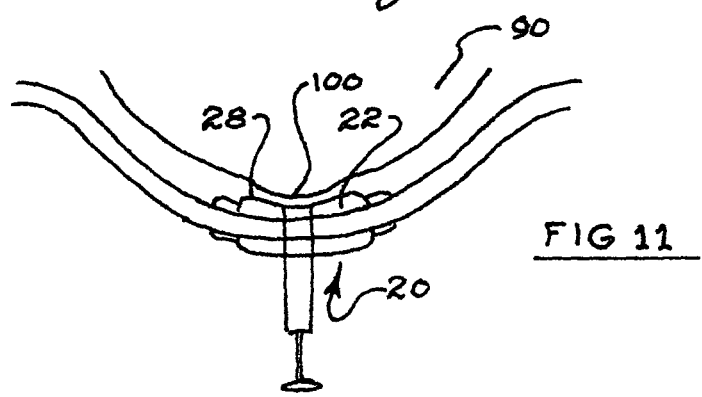
FIG. 11 is a top view drawing of the eye of FIG. 9 showing an eyelid plaque with other limitations.

Referring to FIG. 11, the back surface 28 of the first body 22 may have curvature to match the curvature of the eyeball 90 in the area of the iris 100. As those skilled in the art of eye surgery appreciate, the eyeball is not a perfect sphere and that in the area of the iris there is a "bump" on the eyeball. It is possible that the back surface 28 could have two contours one for the eyeball itself and a second for the iris.

Referring to FIG. 12, the eyelid 88 (lower depicted with upper being similar) has opposed surfaces 104a and b that are not parallel or straight. As a result, there may be an acute angle 106 between the front surface 26 of the first body 22 and the front surface 44 of the second body 24 to accommodate the non-parallel sides of any eyelid 84.

Figure 13:
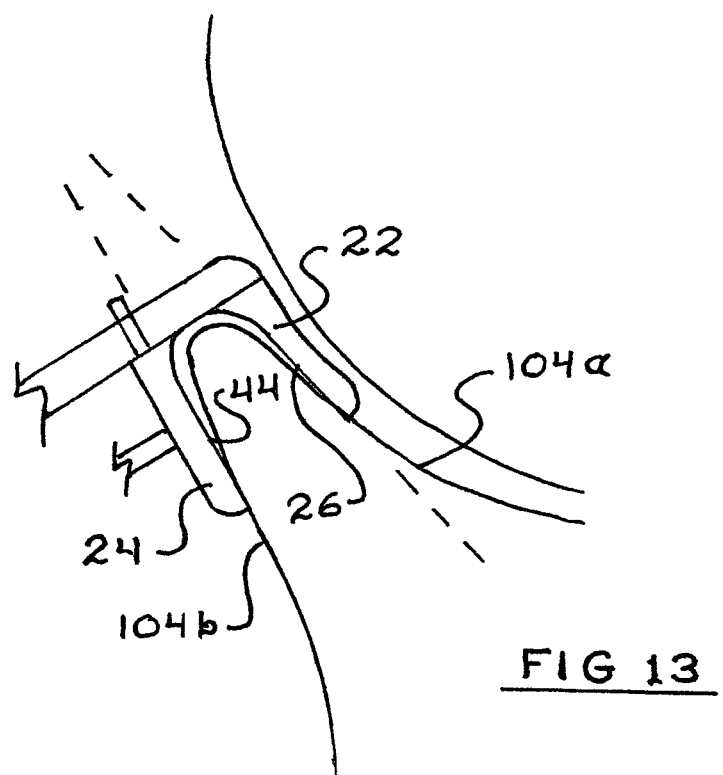
FIG. 13 is a side view drawing of the eye of FIG. 9 showing an eyelid plaque with still other limitations.

Referring to FIG. 13, the front surface 26 of the first body 22 and the front surface 44 of the second body 24 are non-linear such as to accommodate more closely the non-linear aspects of the eyelids.

Where the eyelid plaque 20 is used with eyelids 88, the dimensions of the first body 22 and the second body 24 are based on the size of the cancer and the size of the eyelid. More specifically, the perimeter of the eyelid 88 defines for practical purposes the maximum length of the either the first body 22 or the second body 24. This maximum length of the first and second bodies 22, 24 is thus assumed to be around 25 mm. In addition, as the eyelid 88 must be pulled away from the eyeball 90 for insertion of the first body 22 between the eyelid and the eyeball, that attachment point of the eyeball's muscles on the eyeball defines a gap, thus the maximum thickness of the first body 22, at least from the edge of the eyelid. For use with an upper eyelid 88b, the eyelid plaque 20 is ideally installed with the crease minimized.

As explained above, eyelid cancers are staged, and the staging provides an indication of size. More specifically, T1 stage cancers are 5 mm or smaller in diameter, T2 stage cancers are between 5 mm and 10 mm in diameter, and T3 stage cancers are greater than 10 mm in diameter. Based on these cancer size classifications, the depressions 30, 48 could range from around 5 mm in diameter to 10 mm or larger. The practical maximum for the depressions is the area into which a first body 22 could be placed. More specifically, the area (e.g., gap) under an eyelid 88 represents the practical maximum for the size of the first body 22, which in turn sets the practical maximum for the depression 30 in the first body. It should be appreciated that tumors are rarely round, thus it is the area associated with these measurements that really controls. In addition, this limitation should not be construed as requiring that the depressions 30, 48 necessarily be circular.

An exemplary eyelid plaque 20 could have a first body 22 and a second body 24 with the following approximate dimensions—length 14 mm, height 10 mm and thickness 3 mm. Wherein, a depression within either body defines a rim 32, 50 having a thickness of about 1 mm and a depth of about 2 mm. If an adjustable connection is present, the gap between the first body 22 and the second body 24 should be no less than about 6 mm.

As a final feature, all edges of the eyelid plaque 20, particularly edges that may come in contact the eyeball, should be rounded and smooth. Additionally, it may be desirable to have all, or a portion of, the adjustable connection 60 and stability system 68 removable. More specifically, in use, the first body 22 and second body 24 are attached to the structure, e.g., eyelid, on which the eyelid plaque is being used. Positive attachment, for example by suturing, is desirable to avoid accidental exposure to the radiation during treatment due to shifting of the eyelid plaque 20 or, in the extreme, removal of the plaque. In addition, attachment, for example, by suturing reduces, or eliminates clamping pressure, which could cause damage to the tissues. Removal of the elements of the adjustable connection 60 and/or stability system 68 could be by using temporary attachments for these elements or by designing these structures to be removed by shearing, such as by surgical cutters.

The selection of a radiation source for use in the eyelid plaque 20 is cancer specific. The source can be of any type, such as a single seed, or multiple seeds. The selection of a specific radiation source, its type and placement are well within the knowledge of those skilled in the art. Radioisotopes such as palladium-103, iodine-125, cesium-131, and ruthenium-106 may be used. The use of multiple seeds allows a surgeon to design both the dosage and dosage pattern.

In use, a surgeon examines a patient suspected of having an eyelid cancer. After confirming the presences of an eyelid cancer, the surgeon determines whether the eyelid cancer would be susceptible to treatment using an eyelid plaque 20.

Assuming that the eyelid cancer would be susceptible to treatment with an eyelid plaque 20, the surgeon then selects an appropriate eyelid plaque. Considerations for the proper eyelid plaque 20 include whether treatment is from one side of the eyelid or both, and the size of the bodies of the plaque considering the maximum size possible based on the structure of the eyelid and the minimum size possible based on the size and placement of the eyelid cancer and the amount of radiation required.

As those skilled in the art of treating localized cancers, such as eyelid cancers, the plaque must be of sufficient area to allow for the proper margin of radiation around the cancer. More specifically, the first body 22 and/or second body 24 have depressions. As the radiation source(s) is/are placed within the depression(s), the size of the depression(s) determines the treatment area. The treatment area is at a minimum the size of the cancer. However, an area around the cancer, i.e., a margin, must be maintained to assure the entire cancer is treated.

In addition, the depression(s) must accommodate the radiation source necessary to treat the cancer. Thus, the depth of the first body 22 and/or second body 24 must be proper for the radiation source.

After selecting the eyelid plaque, the surgeon then determines the placement of the radiation source therein. While it is possible to custom design a plaque for a particular eyelid cancer treatment, it is much more likely that eyelid plaques will be available in standard configurations and sizes. Regardless, the surgeon determines the proper placement of the radiation source(s) within the depressions in the first body 22 and/or second body 24.

In this illustrative example, using an eyelid plaque having an adjustable connection having the radiation source therein, the surgeon clamps the eyelid plaque on the eyelid encapsulating the eyelid cancer therein. Then, if attachment points, such as for sutures, are present, the surgeon may suture both the first body 22 and the second body 24 to the eyelid. If sutured, any clamping pressure resulting from the adjustable connection may be released. Then, optionally, the surgeon may remove the adjustable connection.

After the determined treatment period, the eyelid plaque is removed. If the adjustable connection remains, the eyelid plaque may be clamped back onto the eyelid. Then, the sutures if present are removed. Finally, the adjustable connection is released thereby releasing the eyelid plaque from the eyelid, such that the eyelid plaque can be removed.

As those skilled in the art of surgery will appreciate, the above procedure can be altered in many ways to achieve the same result. For example, the adjustable connection need not be present, requiring the individual placement of the first body 22 and second body 24. Additionally, attachment points may be designed for use with something other that sutures.

While there has been illustrated and described what is at present considered to be preferred and alternative embodiments of the claimed invention, it will be appreciated that numerous changes and modifications are likely to occur to those skilled in the art. It is intended in the appended claims to cover all those changes and modifications that fall within the spirit and scope of the claimed invention.

What is claimed is:

1. A method of treating an eyelid cancer comprising the steps of:
   identifying an eyelid cancer susceptible to radiation treatment;
   positioning on the eyelid's tarsal plate a first body and on the eyelid's opposing skin a second body, one of the bodies having a radiation source associated therewith, the first and second body being made of radiation shielding materials such that the bodies act as radiation shields, and the positioning being such that an enclosure about the eyelid cancer is created for confining a significant portion of the radiation therein;
   leaving the first and second body in place for a treatment period; and
   removing the first and second body.

2. The method of claim 1 wherein in the step of positioning on the eyelid's tarsal plate a first body and the eyelid's skin a second body, each body having a radiation source associated therewith.

3. The method of claim 1 wherein in the step of positioning on the eyelid's tarsal plate a first body and the eyelid's skin a second body, the first body and second body are parts of an eyelid plaque wherein the first body is connected to the second body by an adjustable connection permitting controlled movement of the second body as to the first body.

4. The method of claim 3 wherein the adjustable connection has a bar that defines a spatial relationship between the first body and the second body.

* * * * *